US006861068B2

(12) United States Patent
Ng et al.

(10) Patent No.: US 6,861,068 B2
(45) Date of Patent: Mar. 1, 2005

(54) PHARMACEUTICAL COMPOSITIONS USING SEMI-SOLID DELIVERY VEHICLE

(75) Inventors: Steven Y. Ng, San Francisco, CA (US); Hui-Rong Shen, Fremont, CA (US); Jorge Heller, Woodside, CA (US)

(73) Assignee: A.P. Pharma, Inc., Redwood City, CA (US)

( * ) Notice: Subject to any disclaimer, the term of this patent is extended or adjusted under 35 U.S.C. 154(b) by 0 days.

(21) Appl. No.: 10/765,768

(22) Filed: Jan. 26, 2004

(65) Prior Publication Data

US 2004/0156907 A1 Aug. 12, 2004

Related U.S. Application Data

(60) Continuation of application No. 10/409,408, filed on Apr. 7, 2003, now Pat. No. 6,790,458, which is a division of application No. 09/854,180, filed on May 11, 2001, now Pat. No. 6,613,355.
(60) Provisional application No. 60/325,790, filed on May 11, 2000.

(51) Int. Cl.$^7$ ............................. A61K 9/58; A61K 47/30
(52) U.S. Cl. ....................... 424/462; 424/424; 424/425; 424/426; 424/457; 424/486; 525/437; 524/366; 514/772.3; 514/785; 514/786

(58) Field of Search ................................. 424/424, 425, 424/426, 457, 462, 486; 525/437; 524/366; 514/772.3, 785, 786

(56) References Cited

U.S. PATENT DOCUMENTS

| | | | |
|---|---|---|---|
| 4,079,038 A | 3/1978 | Choi et al. | ..................... 260/47 |
| 4,093,709 A | 6/1978 | Choi et al. | ..................... 424/19 |
| 4,131,648 A | 12/1978 | Choi et al. | ..................... 424/22 |
| 4,138,344 A | 2/1979 | Choi et al. | ..................... 252/1 |
| 4,180,646 A | 12/1979 | Choi et al. | .................. 528/153 |
| 4,304,767 A | 12/1981 | Heller et al. | .................. 424/78 |
| 4,946,931 A | 8/1990 | Heller et al. | ................ 528/230 |
| 5,968,543 A | 10/1999 | Heller et al. | ................ 424/425 |

OTHER PUBLICATIONS

Yolles et al. "*Polymer News* " 1: 9–15 (1970).

*Primary Examiner*—Samuel A. Acquah
(74) *Attorney, Agent, or Firm*—Heller Ehrman White & McAuliffe LLP

(57) ABSTRACT

A semi-solid delivery vehicle contains a polyorthoester and an excipient, and a semi-solid pharmaceutical composition contains an active agent and the delivery vehicle. The pharmaceutical composition may be a topical, syringable, or injectable formulation; and is suitable for local delivery of the active agent. Methods of treatment are also disclosed.

19 Claims, No Drawings

PHARMACEUTICAL COMPOSITIONS USING SEMI-SOLID DELIVERY VEHICLE

RELATED APPLICATIONS

This application is a continuation of U.S. application Ser. No. 10/409,408, filed Apr. 7, 2003, now U.S. Pat. No. 6,790,458, which is a divisional of U.S. application Ser. No. 09/854,180, filed May 11, 2001, now U.S. Pat. No. 6,613,355; which claims the priority under 35 USC 119(e) of U.S. Provisional Application No. 60/325,790, filed May 11, 2000.

FIELD

This invention relates to semi-solid delivery vehicles comprising a polyorthoester and an excipient, and to controlled release pharmaceutical compositions comprising the delivery vehicle and an active agent. The pharmaceutical compositions may be in the form of a topical, syringable, or injectable formulation for local controlled delivery of the active agent.

BACKGROUND

A large of class of active agents such as antibiotics, antiseptics, corticosteroids, anti-neoplastics, and local anesthetics may be administered to the skin or mucous membrane by topical application, or by injection. The active agent may act locally or systemically. Topical delivery may be accomplished through the use of compositions such as ointments, creams, emulsions, solutions, suspensions and the like. Injections for delivery of the active agents include solutions, suspensions and emulsions. All of these preparations have been extensively used for delivery of active agents for years. However, these preparations suffer the disadvantage that they are short-acting and therefore they often have to be administered several times in a day to maintain a therapeutically effective dose level in the blood stream at the sites where the activity/treatment is required.

In recent years, a great deal of progress has been made to develop dosage forms which, after their administration, provide a long-term therapeutic response. These products may be achieved by microencapsulation, such as liposomes, microcapsules, microspheres, microparticles and the like. For this type of dosage forms, the active agents are typically entrapped or encapsulated in microcapsules, liposomes or microparticles which are then introduced into the body via injection or in the form of an implant. The release rate of the active agent from this type of dosage forms is controlled which eliminates the need for frequent dosing. However their manufacture is cumbersome which often results in high costs. In addition, they, in many cases, have low reproducibility and consequently lack of reliability in their release patterns. Furthermore, if an organic solvent is used in the manufacturing process, there could be organic solvent residues in the compositions which may be highly toxic. The use of an organic solvent is also undesirable for environmental and fire hazard reasons.

Interest in synthetic biodegradable polymers for the delivery of therapeutic agents began in the early 1970's with the work of Yolles et al., *Polymer News*, 1, 9–15 (1970) using poly(lactic acid). Since that time, numerous other polymers have been prepared and investigated as bioerodible matrices for the controlled release of active agents. U.S. Pat. Nos. 4,079,038, 4,093,709, 4,131,648, 4,138,344, 4,180,646, 4,304,767, 4,946,931, and 5,968,543 disclose various types of biodegradable or bioerodible polymers which may be used for controlled delivery of active agents. Many of these polymers may appear in the form of a semi-solid. However the semi-solid polymer materials are often too sticky. As a result, the active agents frequently cannot be easily and reliably released from the semi-solid polymer materials.

SUMMARY

A first objective of the present invention is to provide a semi-solid delivery vehicle which comprises a polyorthoester and an excipient. The excipient is readily miscible with the polyorthoester and the resulting semi-solid delivery vehicle has a smooth and flowable texture. The polyorthoesters suitable for the invention are represented by formula I and formula II below.

Another objective of the present invention is to provide a controlled release semi-solid pharmaceutical composition for local controlled delivery of an active agent. The composition comprises an active agent and the semi-solid delivery vehicle.

A further objective of the present invention is to provide a semi-solid syringable or injectable composition for the controlled delivery of locally acting active agents, in particular local anesthetics.

The polyorthoester can be homogeneously mixed with the excipient at room temperature without the use of a solvent. The resulting semi-solid delivery vehicle and controlled-release pharmaceutical compositions have a useful texture and viscosity, and the release rate of the active agent from the compositions can also be conveniently and reliably adjusted to accommodate the desired therapeutic effect.

Thus, in a first aspect, this invention is a controlled-release semi-solid pharmaceutical composition comprising:

an active agent; and a semi-solid delivery vehicle, comprising:

a polyorthoester of formula I or formula II

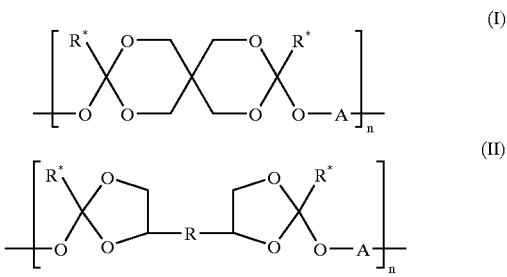

where:

R is a bond, $-(CH_2)_a-$, or $-(CH_2)_b-O-(CH_2)_c-$; where a is an integer of 1 to 10, and b and c are independently integers of 1 to 5;

$R^*$ is a $C_{1-4}$ alkyl;

n is an integer of at least 5; and

A is $R^1$, $R^2$, $R^3$, or $R^4$, where $R^1$ is:

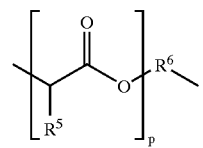

where:
p is an integer of 1 to 20;
$R^5$ is hydrogen or $C_{1-4}$ alkyl; and
$R^6$ is:

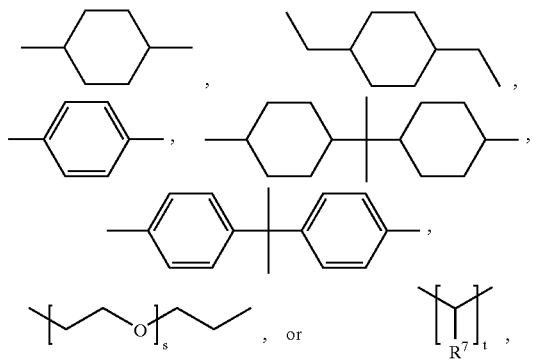

where:
s is an integer of 0 to 30;
t is an integer of 2 to 200; and
$R^7$ is hydrogen or $C_{1-4}$ alkyl;
$R^2$ is:

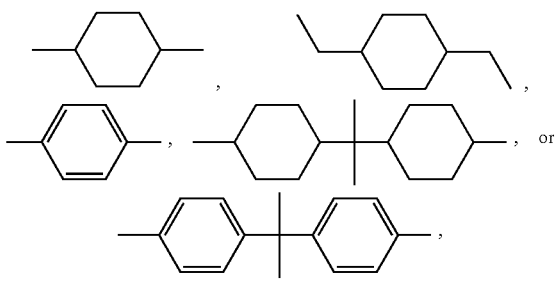

$R^3$ is:

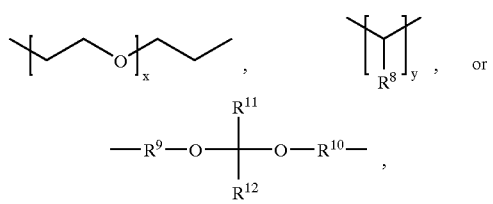

where:
x is an integer of 0 to 30;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is a diol containing at least one functional group independently selected from amide, imide, urea, and urethane groups;
in which at least 0.1 mol percent of the A units are of the formula $R^1$, and
a pharmaceutically acceptable, polyorthoester-compatible liquid excipient selected from polyethylene glycol ether derivatives having a molecular weight between 200 and 4000, polyethylene glycol copolymers having a molecular weight between 400 and 4000, mono-, di-, or tri-glycerides of a $C_{2-19}$ aliphatic carboxylic acid or a mixture of such acids, alkoxylated tetrahydrofurfuryl alcohols and their $C_{1-4}$ alkyl ethers and $C_{2-19}$ aliphatic carboxylic acid esters, and biocompatible oils.

In a second aspect, this invention provides a method of treating a disease state treatable by controlled release local administration of an active agent, in particular treating pain by administration of a local anesthetic, comprising locally administering a therapeutically effective amount of the active agent in the form of the pharmaceutical composition described above.

DETAILED DESCRIPTION

Definitions

Unless defined otherwise in this specification, all technical and scientific terms are used herein according to their conventional definitions as they are commonly used and understood by those of ordinary skill in the art of synthetic chemistry, pharmacology and cosmetology.

"Active agent" includes any compound or mixture of compounds which produces a beneficial or useful result. Active agents are distinguishable from such components as vehicles, carriers, diluents, lubricants, binders and other formulating aids, and encapsulating or otherwise protective components. Examples of active agents are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical incisions) or by injection, such as subcutaneous, intradermal, intramuscular, intraocular, or intra-articular injection. Examples of these agents include, but not limited to, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids, and the like), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors, and the like), cancer chemotherapeutic agents (e.g., mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, and the like), narcotics (e.g., morphine, meperidine, codeine, and the like), local anesthetics (e.g., the amide- or anilide-type local anesthetics such as bupivacaine, dibucaine, mepivacaine, procaine, lidocaine, tetracaine, and the like), antiangiogenic agents (e.g., combrestatin, contortrostatin, anti-VEGF, and the like), polysaccharides, vaccines, antigens, DNA and other polynucleotides, antisense oligonucleotides, and the like. The present invention may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides, and herbicides, plant growth promoters or inhibitors, preservatives, disinfectants, air purifiers and nutrients.

"Alkyl" denotes a linear saturated hydrocarbyl having from one to the number of carbon atoms designated, or a branched or cyclic saturated hydrocarbyl having from three to the number of carbon atoms designated (e.g., $C_{1-4}$ alkyl). Examples of alkyl include methyl, ethyl, n-propyl, isopropyl, cyclopropyl, n-butyl, t-butyl, cyclopropylmethyl, and the like.

"Bioerodible" and "bioerodibility" refer to the degradation, disassembly or digestion of the polyorthoester by action of a biological environment, including the action of living organisms and most notably at physiological pH and temperature. A principal mechanism for bioerosion of the polyorthoesters of the present invention is hydrolysis of linkages between and within the units of the polyorthoester.

"Comprising" is an inclusive term interpreted to mean containing, embracing, covering or including the elements listed following the term, but not excluding other unrecited elements.

"Controlled release", "sustained release", and similar terms are used to denote a mode of active agent delivery that occurs when the active agent is released from the delivery vehicle at an ascertainable and controllable rate over a period of time, rather than dispersed immediately upon application or injection. Controlled or sustained release may extend for hours, days or months, and may vary as a function of numerous factors. For the pharmaceutical composition of the present invention, the rate of release will depend on the type of the excipient selected and the concentration of the excipient in the composition. Another determinant of the rate of release is the rate of hydrolysis of the linkages between and within the units of the polyorthoester. The rate of hydrolysis in turn may be controlled by the composition of the polyorthoester and the number of hydrolysable bonds in the polyorthoester. Other factors determining the rate of release of an active agent from the present pharmaceutical composition include particle size, acidity of the medium (either internal or external to the matrix) and physical and chemical properties of the active agent in the matrix.

"Delivery vehicle" denotes a composition which has the functions including transporting an active agent to a site of interest, controlling the rate of access to, or release of, the active agent by sequestration or other means, and facilitating the application of the agent to the region where its activity is needed.

"Matrix" denotes the physical structure of the polyorthoester or delivery vehicle which essentially retains the active agent in a manner preventing release of the agent until the polyorthoester erodes or decomposes.

"Polyorthoester-compatible" refers to the properties of an excipient which, when mixed with the polyorthoester, forms a single phase and does not cause any physical or chemical changes to the polyorthoester.

"Semi-solid" denotes the mechano-physical state of a material that is flowable under moderate stress. More specifically, the semi-solid material should have a viscosity between about 10,000 and 500,000 cps, especially between about 50,000 and 200,000 cps. Preferably the formulation is easily syringable or injectable, meaning that it can readily be dispensed from a conventional tube of the kind well known for topical or ophthalmic formulations, from a needleless syringe, or from a syringe with an 18 gauge or smaller needle.

"Sequestration" is the confinement or retention of an active agent within the internal spaces of a polyorthoester matrix. Sequestration of an active agent within the matrix may limit the toxic effect of the agent, prolong the time of action of the agent in a controlled manner, permit the release of the agent in a precisely defined location in an organism, or protect unstable agents against the action of the environment.

A "therapeutically effective amount" means the amount that, when administered to an animal for treating a disease, is sufficient to effect treatment for that disease.

"Treating" or "treatment" of a disease includes preventing the disease from occurring in an animal that may bee predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). For the purposes of this invention, a "disease" includes pain.

A "unit" denotes an individual segment of a polyorthoester chain, which consists of the residue of a diketene acetal molecule and the residue of a polyol.

An "α-hydroxy acid containing" unit denotes a unit where A is $R^1$, i.e. in which the polyol is prepared from an α-hydroxy acid or cyclic diester thereof and a diol of the formula HO—$R^5$—OH. The fraction of the polyorthoester that is α-hydroxy acid containing units affects the rate of hydrolysis (or bioerodibility) of the polyorthoester, and in turn, the release rate of the active agent.

Polyorthoesters

The polyorthoesters are of formula I or formula II

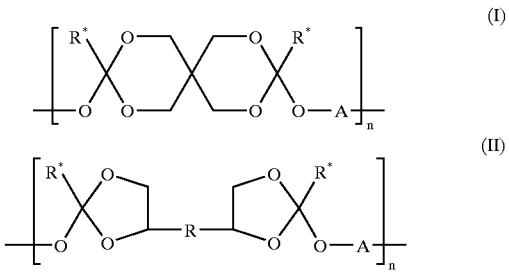

where:

R is a bond, —$(CH_2)_a$—, or —$(CH_2)_b$—O—$(CH_2)_c$—; where a is an integer of 1 to 10, and b and c are independently integers of 1 to 5;

$R^*$ is a $C_{1-4}$ alkyl;

n is an integer of at least 5; and

A is $R^1$, $R^2$, $R^3$, or $R^4$, where $R^1$ is:

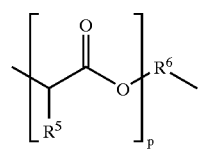

where:

p is an integer of 1 to 20;

$R^5$ is hydrogen or $C_{1-4}$ alkyl; and $R^6$ is:

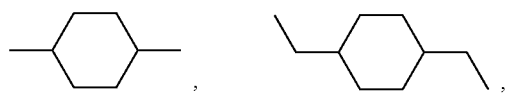

-continued

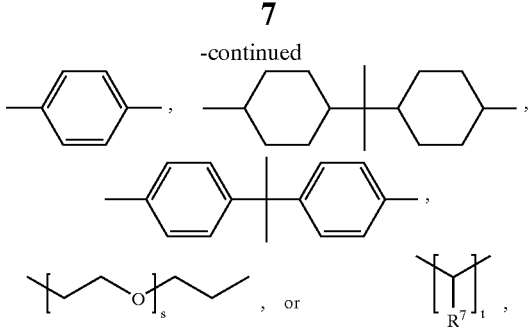

where:
s is an integer of 0 to 30;
t is an integer of 2 to 200; and
$R^7$ is hydrogen or $C_{1-4}$ alkyl;
$R^2$ is:

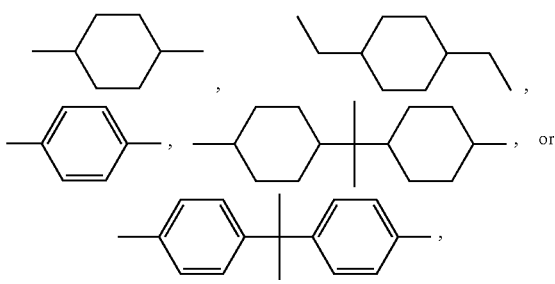

$R^3$ is:

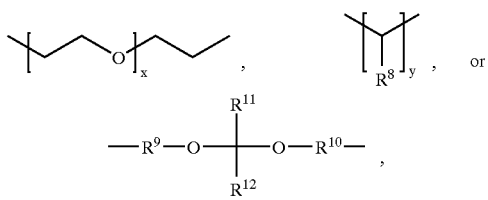

where:
x is an integer of 0 to 30;
y is an integer of 2 to 200;
$R^8$ is hydrogen or $C_{1-4}$ alkyl;
$R^9$ and $R^{10}$ are independently $C_{1-12}$ alkylene;
$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and
$R^4$ is a the residue of a diol containing at least one functional group independently selected from amide, imide, urea, and urethane groups;
in which at least 0.1 mol % of the A units are of the formula $R^1$.

The structure of the polyorthoester useful for the present invention, as shown in formula I and formula II, is one of alternating residues of a diketene acetal and a diol, with each adjacent pair of diketene acetal residues being separated by the residue of one polyol, preferably a diol.

In the presence of water, the α-hydroxyacid containing units are readily hydrolyzed at a body temperature of 37° C. and a physiological pH, to produce the corresponding hydroxyacids. These hydroxyacids then act as acidic catalysts to control the hydrolysis rate of the polyorthoester without the addition of exogenous acid. When the polyorthoester is used as a delivery vehicle or matrix entrapping an active agent, the hydrolysis of the polyorthoester causes release of the active agent.

Polyorthoesters having a higher mole percentage of the "α-hydroxy acid containing" units will have a higher rate of bioerodibility. Preferred polyorthoesters are those in which the mole percentage of the "α-hydroxy acid containing" units is in the range of about 1 to about 50 mole percent, more preferably from about 2 to about 30 mole percent, for example from about 5 to about 30 mole percent, especially from about 10 to about 30 mole percent.

Preferred polyorthoesters are those where:
n is an integer of 5 to 1000;
the polyorthoester has a molecular weight of 1000 to 20,000, preferably 1000 to 10,000, more preferably 1000 to 8000;
$R^5$ is hydrogen or methyl;
$R^6$ is:

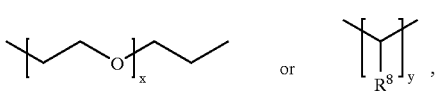

where s is an integer of 0 to 10, especially 1 to 4; s is an integer of 2 to 30, especially 2 to 10; and $R^7$ is hydrogen or methyl;
$R^3$ is:

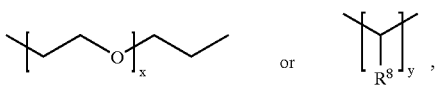

where x is an integer of 0 to 10, especially 1 to 4; y is an integer of 2 to 30, especially 2 to 10; and $R^8$ is hydrogen or methyl;
$R^4$ is selected from the residue of an aliphatic diol of 2 to 20 carbon atoms, preferably 2 to 10 carbon atoms, interrupted by one or two amide, imide, urea, or urethane groups;
the proportion of units in which A is $R^1$ is 1–50 mol %, preferably 2–30 mol %, more preferably 5–30 mol %;
the proportion of units in which A is $R^2$ is less than 20%, preferably less than 10%, especially less than 5%, and
the proportion of units in which A is $R^4$ is less than 20%, preferably less than 10%, especially less than 5%.

While the presence of any of these preferences results in a polyorthoester that is more preferred than the same polyorthoester in which the preference is not met, the preferences are generally independent, and polyorthoesters in which a greater number of preferences is met will generally result in a polyorthoester that is more preferred than that in which a lesser number of preferences is met.

Preparation of the Polyorthoesters

The polyorthoesters are prepared according to the methods described in U.S. Pat. Nos. 4,549,010 and 5,968,543. Specifically, the polyorthoesters are prepared by the reaction of a diketene acetal of formula III or formula IV:

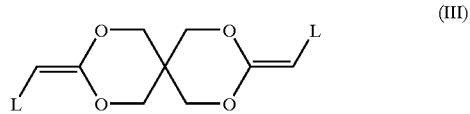

(III)

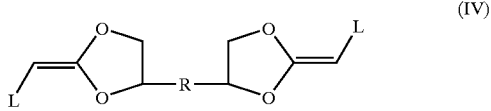

where L is hydrogen or a $C_{1-3}$ alkyl,
with a diol of the formula HO—$R^1$—OH and at least one diol of the formulae HO—$R^2$—OH, HO—$R^3$—OH, and HO—$R^4$—OH.

To form the polyorthoester using a mixture of the two types of the diols, the mixture is formed with selected proportions based on the desired characteristics of the polyorthoester. The use of increasing amounts of diols in which A is $R^1$ increases the bioerodibility of the polyorthoester, and the use of such diols in which $R^6$ is a polyethyleneoxide moiety or an alkane increases the softness of the polymer; the use of increasing amounts of diols in which A is $R^2$ increases the hardness of the polyorthoester (and is therefore not generally desirable, though it may be useful in special circumstances); and the use of diols in which A is $R^3$ increases the softness of the polyorthoester, especially when these diols are low molecular weight polyethylene glycols or aliphatic diols. The use of diols in which A is $R^4$ also generally increases the hardness of the polyorthoester because of the hydrogen bonding between adjacent chains of the polyorthoester, and may or may not be desirable depending on the other diols used.

The preparation of the diketene acetals of the types of formula III and formula IV is disclosed in U.S. Pat. Nos. 4,304,767, 4,532,335, and 5,968,543; and will be known to a person of ordinary skill in the art. A typical method is the condensation of a bis(diol) of formula V (i.e. pentaerythritol) or formula VI:

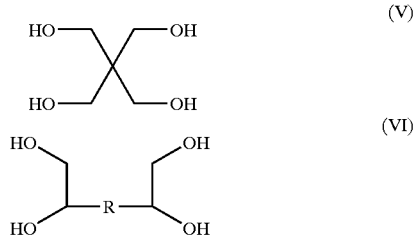

with two equivalents of a 2-halocarboxaldehyde dialkyl acetal, such as 2-bromoacetaldehyde diethyl acetal, followed by dehydrohalogenation to give the diketene acetal. The condensation of a glycol with diethylbromoacetals is described in Roberts et al., *J. Am. Chem. Soc.*, 80, 1247–1254 (1958), and dehydrohalogenation is described in Beyerstedt et al., *J. Am. Chem. Soc.*, 58, 529–553 (1936).

The diketene acetals may also be prepared by the isomerization of divinyl acetals. Thus, for example, 3,9-di(ethylidene)-2,4,8,10-tetraoxaspiro[5.5]undecane (DETOSU) may be prepared by the isomerization of 3,9-divinyl-2,4,8,10-tetraoxaspiro[5.5]undecane, using n-butyllithium in ethylenediamine. The isomerization of the double bond is described in Corey et al., *J. Org. Chem.*, 38, 3224 (1973). The divinyl acetals may be prepared by the condensation of the bis(diol) of formula V or formula VI with two equivalents of a vinylic aldehyde, such as acrolein or crotonaldehyde, or their dialkyl acetals, such as acrolein dimethyl acetal, and such condensation reactions are well known.

The bis(diol) of formula VI where R is a bond is erythritol. The bis(diol) of formula VI where R is —$(CH_2)_a$— may be prepared by the oxidation of an α,ω-diene, such as 1,3-butadiene or 1,5-hexadiene, with an oxidizing reagent such as osmium tetroxide/hydrogen peroxide, or by other methods known in the art, to give the bis(diol). The bis(diol) of formula VI where R is —$(CH_2)_b$—O—$(CH_2)_c$— may be prepared by the reaction of an ω-hydroxy-α-olefin, such as allyl alcohol, with an ω-haloalkyloxirane, such as epichlorohydrin, to form an ω-epoxy-α-olefin with the backbone interrupted by an oxygen atom, such as 2-allyloxymethyloxirane, which is then oxidized with an oxidizing reagent such as osmium tetroxide/hydrogen peroxide, or by other methods known in the art, to give the bis(diol).

The diols of the formulae HO—$R^1$—OH, HO—$R^2$—OH, HO—$R^3$—OH, and HO—$R^4$—OH are prepared according to methods known in the art, and as described, for example, in U.S. Pat. Nos. 4,549,010 and 5,968,543. Some of the diols are commercially available. The diol of the formula HO—$R^1$—OH that comprises a polyester moiety may be prepared by reacting a diol of the formula HO—$R^6$—OH with between 0.5 and 10 molar equivalents of a cyclic diester of an α-hydroxy acid, such as lactide or glycolide, and allowing the reaction to proceed at 100–200° C. for about 12 hours to about 48 hours. Although particular solvents are not required for this reaction, organic solvents such as dimethylacetamide, dimethyl sulfoxide, dimethylformamide, acetonitrile, pyrrolidone, tetrahydrofuran, and methylbutyl ether may be used. The preparation of diols, in particular the diol of the formula HO—$R^3$—OH is generally disclosed in Heller et al., *J. Polymer Sci., Polymer Letters Ed.* 18:293–297 (1980), by reacting an appropriate divinyl ether with an excess of an appropriate diol. Diols of the formula HO—$R^4$—OH include diols where $R^4$ is R'CONR"R' (amide), R'CONR"COR' (imide), R'NR"CONR"R' (urea), and R'OCONR"R' (urethane), where each R' is independently an aliphatic, aromatic, or aromatic/aliphatic straight or branched chain hydrocarbyl, especially a straight or branched chain alkyl of 2 to 22 carbon atoms, especially 2 to 10 carbon atoms, and more especially 2 to 5 carbon atoms, and R" is hydrogen or $C_{1-6}$ alkyl, especially hydrogen or methyl, more especially hydrogen. Some representative diols of the formula HO—$R^4$—OH include N,N'-bis-(2-hydroxyethyl)terephthalamide, N,N'-bis-(2-hydroxyethyl)pyromellitic diimide, 1,1'-methylenedi(p-phenylene)bis-[3-(2-hydroxyethyl)urea], N,N'-bis-(2-hydroxyethyl)oxamide, 1,3-bis(2-hydroxyethyl)urea, 3-hydroxy-N-(2-hydroxyethyl)-propionamide, 4-hydroxy-N-(3-hydroxypropyl)butyramide, and bis(2-hydroxyethyl) ethylenedicarbamate. These diols are known to the art in reported syntheses and may are commercially available. Representative diols of the formula HO—$(CH_2)_n$—NHCO—$(CH_2)_m$—OH where n is an integer of 2 to 6 and m is an integer of 2 to 5 are made by the reaction of 2-aminoethanol, 3-aminopropanol, 4-aminobutanol, 5-aminopentanol, or 6-aminohexanol with β-propiolactone, γ-butyrolactone, δ-valerolactone, or ε-caprolactone. Representative diols of the formula HO—$(CH)_n$—NHCOO—$(CH_2)_m$—OH where n and m are each integers of 2 to 6 are made by the reaction of the same aminoalcohols just mentioned with cyclic carbonates of the formula

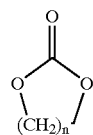

such as ethylene carbonate. Bis-amide diols of the formula HO-A-NHCO-B-CONH-A-OH are prepared by the reaction of a diacid, optionally in activated form, such as the diacyldihalide, with two equivalents of a hydroxy-amine. Other methods of preparation of the diols of the formula HO—R$^4$—OH are known in the art.

Once made, the diol of the formula HO—R$^1$—OH and the diol(s) of the formulae HO—R$^2$—OH, HO—R$^3$—OH, and HO—R$^4$—OH in the desired proportions are mixed with the diketene acetal of formula III or formula IV, in a slightly less than 1:1 (e.g. 0.5:1–0.9:1) ratio of total number of moles of diketene acetal to total number of moles of diols, in a suitable solvent at ambient temperature. The condensation reaction between the diketene acetal and the diols is carried out under conditions which are described in, for example, U.S. Pat. Nos. 4,304,767, 4,549,010, and 5,968,543, and are well known to those skilled in the art; and will also be readily apparent from the structures of the reactants themselves. Suitable solvents are aprotic solvents, such as dimethylacetamide, dimethyl sulfoxide, dimethylformamide, acetonitrile, acetone, ethyl acetate, pyrrolidone, tetrahydrofuran, and methylbutyl ether, and the like. Catalysts are not required for this reaction, but when used, suitable catalysts are iodine in pyridine, p-toluenesulfonic acid; salicylic acid, Lewis acids (such as boron trichloride, boron trifluoride, boron trichloride etherate, boron trifluoride etherate, stannic oxychloride, phosphorus oxychloride, zinc chloride, phosphorus pentachloride, antimony pentafluoride, stannous octoate, stannic chloride, diethyl zinc, and mixtures thereof); and Brønsted catalysts (such as polyphosphoric acid, crosslinked polystyrene sulfonic acid, acidic silica gel, and mixtures thereof). A typical amount of catalyst used is about 0.2% by weight relative to the diketene acetal. Smaller or larger amounts can also be used, such as 0.005% to about 2.0% by weight relative to the diketene acetal. Once the reaction is complete, the reaction mixture is allowed to cool and concentrated by rotoevaporation under vacuum. The concentrated mixture may be further dried under vacuum at an elevated temperature.

The polyorthoesters may also be prepared by reaction of the diketene acetal with the chosen diol(s) under similar reaction conditions, but in the presence of a "chain stopper" (a reagent that terminates polyorthoester chain formation. Suitable chain stoppers are C$_{5-20}$ alkanols, especially C$_{10-20}$ alkanols. The chain stopper is preferably present in from 1–20 mol % based on the diketene acetal. The polyorthoesters thus prepared have low molecular weights with a lower molecular weight dispersion than those prepared by the reaction of the diketene acetals with only diols, and are therefore especially suitable for this invention.

The Excipients

The excipients suitable for the present invention are pharmaceutically acceptable and polyorthoester-compatible materials. They are liquid at room temperature, and are readily miscible with the polyorthoesters.

Suitable excipients include poly(ethylene glycol) ether derivatives having a molecular weight of between 200 and 4,000, such as poly(ethylene glycol) mono- or di-alkyl ethers, preferably poly(ethylene glycol)monomethyl ether 550 or poly(ethylene glycol)dimethyl ether 250; poly (ethylene glycol) copolymers having a molecular weight of between 400 and 4,000 such as poly(ethylene glycol-co-polypropylene glycol); propylene glycol mono- or di-esters of a C$_{2-19}$ aliphatic carboxylic acid or a mixture of such acids, such as propylene glycol dicaprylate or dicaprate; mono-, di- or tri-glycerides of a C$_{2-19}$ aliphatic carboxylic acid or a mixture of such acids, such as glyceryl caprylate, glyceryl captate, glyceryl caprylate/caprate, glyceryl caprylate/caprate/laurate, glycofurol and similar ethoxylated tetrahydrofurfuryl alcohols and their C$_{1-4}$ alkyl ethers and C$_{2-19}$ aliphatic carboxylic acid esters; and biocompatible oils such as sunflower oil, sesame oil and other non- or partially-hydrogenated vegetable oils.

Most of these materials are commercially available, for example, from Aldrich Chemical Company (Milwaukee, Wis.) and from Abitec Corporation (Columbus, Ohio), LIPO Chemicals Inc. (Paterson, N.J.), and Jarchem Industries, Inc. (Newark, N.J.).

The Delivery Vehicle

The delivery vehicle comprises a polyorthoester and an excipient selected from those described in preceding sections.

The concentrations of the polyorthoester and the excipient in the delivery vehicle may vary. For example, the concentration of the excipient in the vehicle may be in the range of 1–99% by weight, preferably 5–80% weight, especially 25–60% by weight of the vehicle.

While the singular form is used to describe the polyorthoester and excipient in this application, it is understood that more than one polyorthoesters and excipients selected from the groups described above may be used in the delivery vehicle.

The delivery vehicle is prepared by mixing or blending together the polyorthoester and the excipient. The mixing or blending can be performed by any methods at a temperature less than about 50° C., e.g. at room temperature, in the absence of solvents, using any suitable devices to achieve a homogeneous, flowable and non-tacky semi-solid blend at room temperature.

Semi-Solid Pharmaceutical Compositions

If the active agent is itself a liquid or semi-solid, it may be mixed with the delivery vehicle in the same manner as the delivery vehicle was formed, i.e. conventional blending of semi-solid formulations. However, the active agent is typically a solid. It is desirable that the particle size of the active agent be sufficiently small (for example, 1–100 μm, especially 5–50 μm) so that the resulting composition is smooth. Therefore, unless the active agent is already in micron-sized powder form, it is generally first milled into fine particles preferably less than 100 μm and sieved before mixing with the other ingredients. The mechanical mixing process is performed at room temperature, preferably under vacuum in order to avoid air bubbles. Further size reduction of the size of the particles of the active agent can be carried out by passing the semi-solid mixture through a ball mill or roller mill to achieve a homogeneous and uniform pharmaceutical composition.

The active agent may be mixed with the delivery vehicle already formed or directly mixed together with the polyorthoester and the excipient.

The active agent is present in the composition in an amount which is effective to provide a desired biological or therapeutic effect. Because of the sustained release nature of the compositions, the active agent usually is present in an amount which is greater than the conventional single dose. The concentration of the active agent in the semi-solid polyorthoester composition can vary over a wide range (e.g., 0.1–80 wt. %, preferably 1–60 wt. %, more preferably 2–40 wt. %, such as 5–30 wt. %, based on the composition as a whole) depending on a variety of factors, such as the release profile of the composition, the therapeutically effective dose of the active agent, and the desired length of the time period during which the active agent is released.

The concentration of the polyorthoester may be 1–99 wt. %, preferably 5–40 wt. %, of the composition. The total concentration of the excipient is 1–90 wt. %, preferably 5–60 wt. %, more preferably 10–50 wt. %, of the composition.

It is also understood that while not required, other pharmaceutically acceptable inert agents such as coloring agents and preservatives may also be incorporated into the composition.

The semi-solid pharmaceutical composition of the present invention has an improved texture which is non-tacky and flowable. The composition therefore can be conveniently applied to the skin or mucous membrane in the manner of a convention al cream or gel. Preferably the formulation is easily syringable or injectable, meaning that it can readily be dispensed from a conventional tube of the kind well known for topical or ophthalmic formulations, from a needleless syringe, or from a syringe with an 18 gauge or smaller needle, and injected subcutaneously, intradermally or intramuscularly.

After topical application or administration by injection, the active agent is released from the composition in a sustained and controlled manner. The rate of release may be regulated or controlled in a variety of ways to accommodate the desired therapeutic effect. The rate may be increased or decreased by altering the mole percentage of the α-hydroxy acid containing units in the polyorthoester, or by selecting a particular excipient, or by altering the amount of the selected excipient, or the combination thereof.

The compositions are also stable. The release rates of the active agent are not affected by irradiation for sterilization.

Particular Compositions and their Uses

Exemplary compositions of this invention, and their uses, include:

compositions containing local anesthetics, optionally in combination with glucocorticosteroids such as dexamethasone, cortisone, hydrocortisone, prednisone, prednisolone, beclomethasone, betamethasone, flunisolide, fluocinolone acetonide, fluocinonide, triamcinolone, and the like, for the prolonged relief of local pain or a prolonged nerve blockade. This use is discussed further below;

compositions containing cancer chemotherapeutic agents, such as those listed above under "Active Agents", for deposition by syringe or by injection into tumors or operative sites from which a tumor has been ablated, for tumor control or treatment and/or the suppression of regrowth of the tumor from residual tumor cells after ablation of the tumor;

compositions containing progestogens, such as flurogestone, medroxyprogesterone, norgestrel, norgestimate, norethindrone, and the like, for estrus synchronization or contraception;

compositions containing antimetabolites such as fluorouracil and the like, as an adjunct to glaucoma filtering surgery; compositions containing antiangiogenic agents such as combrestatin, for the treatment of macular degeneration and retinal angiogenesis; and other compositions for the controlled release of ophthalmic drugs to the eye;

compositions containing therapeutic polypeptides (proteins), such as insulin, LHRH antagonists, and the like, for the controlled delivery of these polypeptides, avoiding the need for daily or other frequent injection;

compositions containing anti-inflammatory agents such as the NSAIDs, e.g. ibuptofen, naproxen, COX-1 or COX-2 inhibitors, and the like, or glucocorticosteroids, for intra-articular injection;

compositions containing antibiotics, for the prevention or treatment of infection, especially for deposition into surgical sites to suppress post-operative infection, or into or on wounds, for the suppression of infection (e.g. from foreign bodies in the wound);

compositions containing morphogenic proteins such as bone morphogenic protein; and compositions containing DNA or other polynucleotides, such as antisense oligonucleotides.

Delivery of Controlled-release Local Anesthetics by Injection

Local anesthetics induce a temporary nerve conduction block and provide pain relief which lasts from a few minutes to a few hours. They are frequently used to prevent pain in surgical procedures, dental manipulations or injuries.

The synthetic local anesthetics may be divided into two groups: the slightly soluble compounds and the soluble compounds. Conventionally, the soluble local anesthetics can be applied topically and by injection, and the slightly soluble local anesthetics are used only for surface application. The local anesthetics conventionally administered by injection can also be divided into two groups, esters and non-esters. The esters include (1) benzoic acid esters (piperocaine, meprylcaine and isobucaine); (2) para-aminobenzoic acid esters (procaine, tetracaine, butethamine, propoxycaine, chloroprocaine); (3) meta-aminobenzoic acid esters (metabutethamine, primacaine); and (4)para-ethoxybenzoic acid ester (parethoxycaine). The non-esters are anilides (amides or non-esters) which include bupivacaine, lidocaine, mepivacaine, pyrrocaine and prilocalne.

Many of the local anesthetics are conventionally used in the form of their acid addition salts, as this provides solubility in aqueous injection media. However, because the presence of the large amount of acid within such a local anesthetic acid addition salt will result in more rapid degradation of the polyorthoesters and release of the local anesthetic, it is generally desirable to use the local anesthetics in free base form, or with only a small proportion of the acid addition salt present (addition of small quantities of the acid addition salt may provide enhanced release if desired).

The semi-solid injectable form of a local anesthetic of the present invention is prepared by incorporating the local anesthetic into the delivery vehicle in a manner as described above. The concentration of the local anesthetic may vary from 1–60 wt. %, preferably 5–30 wt. %, e.g. about 10 wt. %. The semi-solid composition is then filled into a syringe with a 18–25 gauge needle, and injected into sites that are painful or to be subjected to surgical procedures. The semi-solid injectable composition of the present invention can be used for controlled delivery of both slightly soluble and soluble local anesthetics.

Because the duration of action of a local anesthetic is proportional to the time during which it is in actual contact with nervous tissues, the present injectable delivery system can maintain localization of the anesthetic at the nerve for an extended period of time which will greatly prolong the effect of the anesthetic.

A number of authors, including Berde et al., U.S. Pat. No. 6,046,187 and related patents, have suggested that the co-administration of a glucocorticosteroid may prolong or otherwise enhance the effect of local anesthetics, especially controlled-release local anesthetics; and formulations containing a local anesthetic and a glucocorticosteroid, and their uses for controlled release local anesthesia, are within the scope of this invention.

EXAMPLES

Example 1

Preparation of Polyorthoesters

The following syntheses illustrate the preparation of representative polyorthoesters. The starting materials are either commercially available or may be prepared as described in the preceding sections and in U.S. Pat. Nos. 4,549,010 and 5,968,543.

1(a) The polyorthoester in this example was prepared from 3,9-di(ethylidene)-2,4,8,10-tetraoxaspiro[5.5] undecane (DETOSU), triethylene glycol (TEG), and triethyleneglycol monoglycolide (TEG-mGL). The molar ratio of the three components (DETOSU:TEG:TEG-mGL) was 65:95:5.

Under rigorously anhydrous conditions, DETOSU (6.898 g, 32.5 mmol), TEG (7.133 g, 47.5 mmol) and TEG-mGL (0.521 g, 2.5 mmol) were weighed into a 250 mL round bottom flask, and the mixture dissolved in anhydrous ethyl acetate (16 mL). To this solution was added a salicylic acid solution in ethyl acetate (12 drops, 10 mg/mL) to initiate the polymerization. The solution came to a boil within a few minutes. The solution was allowed to cool to room temperature, then concentrated by rotoevaporation at 40–50° C. The flask was transferred to a vacuum oven, and dried at 40° C. for 2 hours followed by drying at 70° C. for additional 3 hours. The material was semi-solid with a molecular weight of about 4000.

1(b) The polyorthoester in this example was prepared from DETOSU, TEG, and triethyleneglycol diglycolide (TEG-diGL). The molar ratio of the three components (DETOSU:TEG:TEG-diGL) was 65:80:20. Following the procedure of Example 1(a), DETOSU (6.898 g, 32.5 mmol), TEG (6.007 g, 40 mmol) and TEG-diGL (2.662 g, 10 mmol) were allowed to react. The reaction yielded a semi-solid material having a molecular weight of about 2000.

1(c) The polyorthoester in this example was prepared from DETOSU, TEG, and TEG-diGL. The molar ratio of the three components (DETOSU:TEG:TEG-diGL) was 60:70:30. Following the procedure of Example 1(a), DETOSU (25.470 g, 120 mmol), TEG (21.024 g, 140 mmol) and TEG-diGL (15.973 g, 60 mmol) were allowed to react. The reaction yielded a semi-solid material having a molecular weight of about 2000.

Other polyorthoesters, e.g. those containing diketene acetals of formula IV and/or those containing other diols of formulae HO—$R^1$—OH, HO—$R^2$—OH, HO—$R^3$—OH, and HO—$R^4$—OH, are prepared by similar methods.

Example 2

Preparation of Pharmaceutical Compositions

Semi-solid pharmaceutical compositions with bupivacame as the active agent were prepared by first milling the bupivacaine into fine particles and sieving, before mixing with selected amounts of a polyorthoester and an excipient. The mixing process was performed at room temperature under vacuum. Further size reduction of the bupivacaine particles was carried out by passing the semi-solid composition through a ball mill.

A. 60 wt. % polyorthoester (DETOSU/TEG/TEG-mGL 60:95:5) 40 wt. % bupivacaine. (control)

B. 40 wt. % polyorthoester (DETOSU/TEG/TEG-mGL 60:95:5) 40 wt. % bupivacaine 20 wt. % polyethylene glycol monomethyl ether 550.

C. 60 wt. % polyorthoester (DETOSU/TEG/TEG-diGL 60:80:20) 40 wt. % bupivacaine. (control)

D. 40 wt. % polyorthoester (DETOSU/TEG/TEG-diGL 60:80:20) 40 wt. % bupivacaine 20% wt. % polyethylene glycol monomethyl ether 550.

E. 20% wt. % polyorthoester (DETOSU/TEG/TEG-diGL 60:70:30) 40% wt. % bupivacaine 40% wt. % polyethylene glycol monomethyl ether.

Compositions B, D, and E had non-tacky, flowable texture. Compositions A and C had very sticky texture, were difficult to handle and showed poor syringability.

Other compositions containing other polyorthoesters, e.g. those containing diketene acetals of formula IV and those containing other diols of formulae HO—$R^1$—OH, HO—$R^2$—OH, HO—$R^3$—OH, and HO—$R^4$—OH, and different active agents, and/or in different proportions are prepared in a similar manner.

Example 3

Release Profiles of the Pharmaceutical Compositions

The semi-solid compositions of Example 2 were weighed, placed into bottles with screw caps. 100 mL of 50 mM PBS (pH 7.4) was added to each bottle. The test bottles were transferred to a 37° C. incubator and placed on top of a rotor shaker (36 rpm). At various time points, bottles were removed from the incubator and samples of about 5 mL were removed and analyzed for bupivacaine content by HPLC at 263 nm. The remaining volume of buffer was removed and replaced with 100 mL fresh buffer.

Composition B had an increased rate of release over the control Composition A.

Composition D had a similar release rate as the control Composition C.

These test results demonstrated that the pharmaceutical compositions of the present invention have the advantage that the release rates of the composition may be adjusted and controlled in a variety of ways. The rates of release can be adjusted to accommodate a desired therapeutic effect by either altering the mole percentage of the α-hydroxyacid containing units in the polyorthoester as disclosed in U.S. Pat. No. 5,968,543, or by selecting a particular excipient, or by altering the concentration of the excipient in the composition, or the combination of all these factors.

The compositions can be irradiated, and the release rate of Composition E before and after irradiation showed no significant difference over twelve days using the test described above.

The foregoing is offered primarily for purposes of illustration. It will be readily apparent to those skilled in the art that the molecular structures, proportions of the various components in the delivery vehicle or pharmaceutical composition, method of manufacture and other parameters of the invention described herein may be further modified or substituted in various ways without departing from the spirit and scope of the invention.

What is claimed is:

1. A pharmaceutical composition, comprising:

an active agent selected from mepivacaine, bupivacaine, dibucaine, procaine, lidocaine, tetracaine, antibiotics, antivirals, fungicides, scabicides or pediculicides, benzalkonium chloride, benzethonium chloride, chlorhexidine gluconate, mafenide acetate, methylbenzethonium chloride, nitrofurazone, nitromersol, estrogens, progestins, androgens, adrenocorticoids, insulin, erythropoietin, morphogenic proteins, bone morphogenic protein, aspirin, ibuprofen, naproxen, ketorolac, COX-1 inhibitors, COX-2 inhibitors, mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen, morphine, meperidine, codeine, combrestatin, contortrostatin, anti-VEGF, astringents, antiperspirants, irritants, rubefacients, vesicants, sclerosing agents, caustics, escharotics, keratolytic agents, sunscreens, hypopigmenting and antipruritic agents, fungicides, pesticides, herbicides, plant growth promoters or inhibitors, preservatives, disinfectants, air purifiers, nutrients, dexamethasone, cortisone, hydrocortisone, prednisone, prednisolone, beclomethasone, betamethasone, flunisolide, fluocinolone acetonide, fluocinonide, triamcinolone, flurogestone, medroxyprogesterone, norgestrel, norgestimate, norethindrone, fluorouracil and LHRH antagonists; and a semi-solid delivery vehicle comprising:

a polyorthoester of formula I or formula II

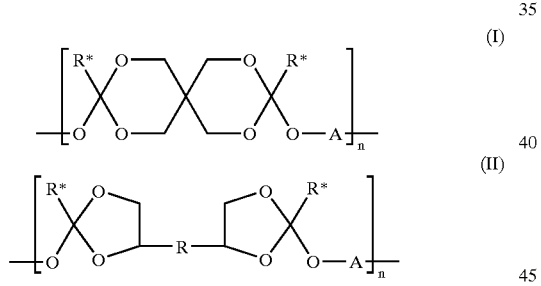

where:

R is a bond, —$(CH_2)_a$—, or —$(CH_2)_b$—O—$(CH_2)_c$—; where a is an integer of 1 to 10, and b and c are independently integers of 1 to 5;

R* is a $C_{1-4}$ alkyl;

n is an integer of at least 5; and

A is $R^1$, $R^2$, $R^3$, or $R^4$, where $R^1$ is:

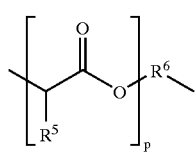

where:

p is an integer of 1 to 20;

$R^5$ is hydrogen or $C_{1-4}$ alkyl; and $R^6$ is:

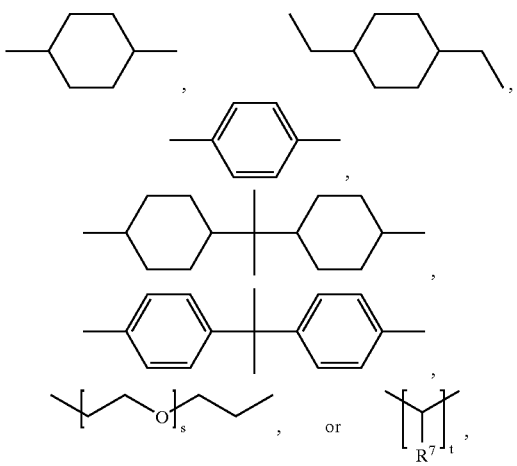

where:

s is an integer of 0 to 30;

t is an integer of 2 to 200; and $R^7$ is hydrogen or $C_{1-4}$ alkyl;

$R^2$ is:

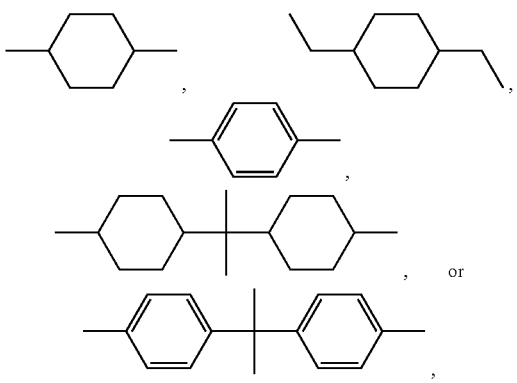

$R^3$ is:

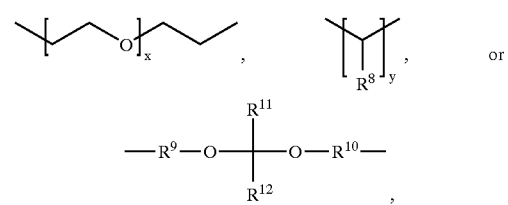

where:

x is an integer of 0 to 30;

y is an integer of 2 to 200;

$R^8$ is hydrogen or $C_{1-4}$ alkyl;

$R^9$ and $R^{10}$ are independently $C_{1-12}$ alkylene;

$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and $R^4$ is a diol containing at least one functional group independently selected from armide, imide, urea, and urethane groups;

in which at least 0.1 mol percent of the A units are of the formula $R^1$, and a pharmaceutically acceptable, polyorthoester-compatible liquid excipient selected from polyethylene glycol ether derivatives having a molecular weight between 200 and 4000, polyethylene glycol copolymers having a molecular weight between 400 and 4000, mono-, di-, or tri-glycerides of a $C_{2-19}$ aliphatic carboxylic acid or a mixture of such acids, alkoxylated tetrahydrofurfuryl alcohols and their $C_{1-4}$ alkyl ethers and $C_{2-19}$ aliphatic carboxylic acid esters, and biocompatible oils.

2. The composition of claim 1, wherein the active agent is mepivacaine.

3. The composition of claim 2 where the concentration of the polyorthoester ranges from 1% to 99% by weight of the delivery vehicle.

4. The composition of claim 2 where the polyorthoester has a molecular weight between 1000 and 20,000.

5. The composition of claim 2 where the fraction of the A units that are of the formula $R^1$ is between 1 and 90 mol percent.

6. The composition of claim 2 where the polyorthoester is of formula I, where:
none of the units have A equal to $R^2$;
$R^3$ is:

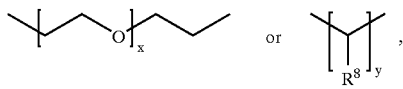

where:
x is an integer of 0 to 10;
y is an integer of 2 to 30; and
$R^6$ is:

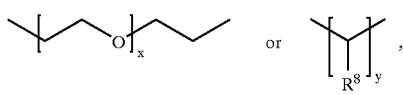

where:
s is an integer of 0 to 10;
t is an integer of 2 to 30; and
$R^5$, $R^7$, and $R^8$ are independently hydrogen or methyl.

7. The composition of claim 6 where:
$R^3$ and $R^6$ are both —$(CH_2$—$CH_2$—$O)_2$—$(CH_2$—$CH^2)$—;
$R^5$ is methyl; and
p is 1 or 2.

8. The composition of claim 6 where:
$R^3$ and $R^6$ are both —$(CH_2$—$CH_2$—$O)_9$—$(CH_2$—$CH_2)$—;
$R^5$ is methyl; and
p is 1 or 2.

9. The composition of claim 2 where the fraction of the active agent is from 1% to 60% by weight of the composition.

10. The composition of claim 9 where the fraction of the active agent is from 5% to 30% by weight of the composition.

11. The composition of claim 2 where the composition is in topical, syringable, or injectable form.

12. A method of treating a disease state treatable by controlled release local administration of an active agent, comprising locally administering a therapeutically effective amount of the active agent in the form of a pharmaceutical composition of claim 1.

13. The method of claim 12 where the active agent is mepivacaine.

14. A method of preventing or relieving local pain at a site in a mammal, comprising administering to the site a therapeutically effective amount of a local anesthetic in the form of a pharmaceutically acceptable composition of claim 2.

15. A method of preventing or relieving local pain at a site in a mammal, comprising administering to the site a therapeutically effective amount of a local anesthetic in the form of a pharmaceutically acceptable composition of claim 9.

16. A process for the preparation of the pharmaceutical composition of claim 1 where the active agent is in solid form, comprising:
optionally milling the active agent to reduce the particle size of the active agent;
mixing the active agent and the delivery vehicle; and
optionally milling the composition to reduce the particle size of the active agent.

17. The composition of claim 2, wherein the excipient is poly(ethylene glycol)monomethyl ether 550.

18. The composition of claim 2, wherein the excipient is a polyethylene glycol ether derivative having a molecular weight between 200 and 4000.

19. A method of preventing or relieving local pain at a site in a mammal, comprising administering to the site a therapeutically effective amount of a local anesthetic in the form of a pharmaceutically acceptable composition of claim 17.

* * * * *